United States Patent [19]

Beane et al.

[11] 4,237,897
[45] Dec. 9, 1980

[54] BATTERY LIFE EXTENDER

[75] Inventors: Russell R. Beane, Sepulveda; Brian M. Mann, Northridge, both of Calif.

[73] Assignee: Pacesetter Systems, Inc., Sylmar, Calif.

[21] Appl. No.: 957,411

[22] Filed: Nov. 3, 1978

[51] Int. Cl.³ .............................................. D61N 1/36
[52] U.S. Cl. .......................................... 128/419 PG
[58] Field of Search .................... 128/419 PS, 419 PG

[56] References Cited

U.S. PATENT DOCUMENTS

| | | | |
|---|---|---|---|
| 3,669,120 | 6/1972 | Nielsen | 128/419 PG |
| 3,842,844 | 10/1974 | Alferness | 128/419 PG |
| 3,901,247 | 8/1965 | Walmsley | 128/419 PG |
| 4,095,603 | 6/1978 | Davies | 128/419 PG |
| 4,120,306 | 10/1978 | Renirie | 128/419 PS |

Primary Examiner—William E. Kamm
Attorney, Agent, or Firm—Freilich, Hornbaker, Wasserman, Rosen & Fernandez

[57] ABSTRACT

A battery life extender for use in an implantable tissue stimulator. The tissue stimulator comprises a battery which powers a volatile memory, control circuits and a pulse output circuit all of which are connected in parallel across the battery. The invention provides a means for controlling current through the output circuit as a function of a difference voltage between the battery output voltage and a reference voltage. The reference voltage and battery voltage comprise inputs to a differential amplifier which in turn provides an output control voltage which controls a field-effect transistor (FET) connected in series with the output circuit and battery. As this control voltage rises, current through the field-effect transistor is reduced, thereby reducing the amplitude of the pulses from the output circuit and the current drain from the battery. This keeps the battery output voltage high and maintains a more nearly constant voltage on the volatile memory and control circuits for a longer period of time than would otherwise be available.

15 Claims, 4 Drawing Figures

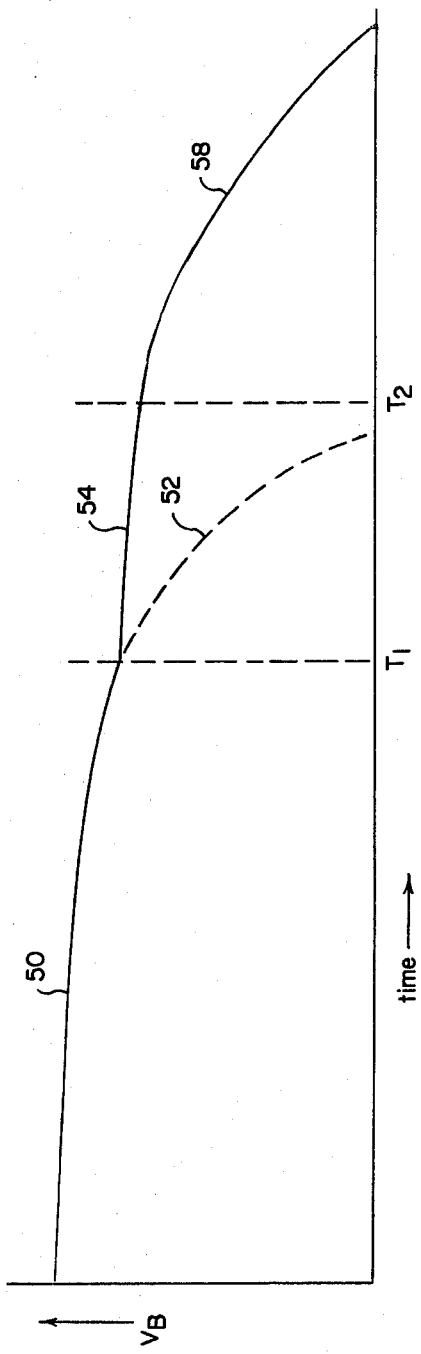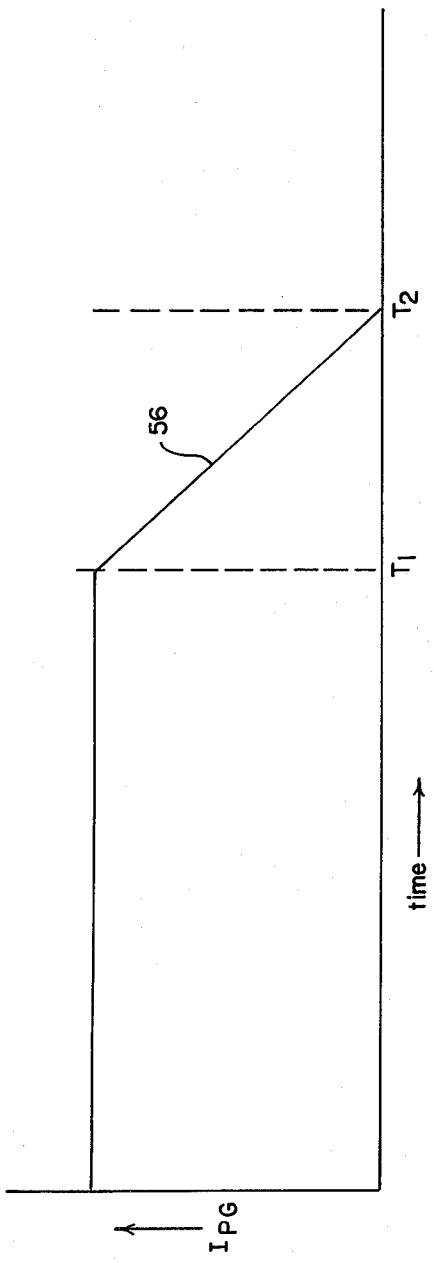

BATTERY LIFE EXTENDER

FIELD OF THE INVENTION

The invention relates to circuitry for extending the life of a battery in an implantable tissue stimulator and more particularly to circuitry which selectively controls current through one portion of the stimulator as a function of battery output voltage.

BACKGROUND OF THE INVENTION

A typical implantable tissue stimulator such as a device for electrically stimulating the heart at predetermined time intervals comprises a battery, an output circuit for providing tissue stimulation pulses and a volatile memory and control circuit for controlling frequency and other parameters provided by the tissue stimulator. It is well known in the medical sciences that the frequency provided by a tissue stimulator is extremely critical to the health of a patient. In programmable tissue stimulators these pulses are controlled by a programmable memory which contains information predetermined with respect to pulse requirements of a particular patient. A problem with these system utilizing a volatile memory is that the information contained therein can be affected if the battery voltage drops below a certain critical level, this altered information having a deleterious effect on a patient due to its control of the tissue stimulation pulse characteristics. Conventional tissue stimulators have attempted to alleviate the problem in several ways, one of which has been to inactivate the output circuit if the battery output voltage falls below a predetermined level. However this results in an immediate removal of pulses which in severe cases could result in extreme discomfort and even death to the patient prior to the time that the battery could be removed and replaced.

SUMMARY OF THE INVENTION

The present invention solves the above problems by providing circuitry whereby a substantially constant voltage is supplied to the volatile memory for a longer period of time by gradually reducing the amplitude of output pulses from the output circuit, thereby taking advantage of a safety factor associated with selection of a suitable pulse amplitude.

In an electronic circuit having a voltage source driving a first load impedance and a second load impedance in parallel with the first load impedance, the invention provides a means for generating a reference voltage, a means for providing a control voltage related to a voltage difference between the reference voltage and the source voltage, and a means for controlling current through the second load impedance as a function of the value of the control voltage. In a specific embodiment, the electronic circuit is contained within an implantable tissue stimulator, the voltage source is a battery, the first load impedance is a volatile programmable memory and control circuity, and the second load impedance is an output circuit. The reference voltage is generated by an appropriate circuit and the control voltage is obtained from the output of a differential amplifier having the reference voltage and a predetermined fraction of the battery voltage as inputs. The control voltage output is applied to the gate or control electrode of a field-effect transistor (FET) connected in series with the second load impedance so that as the control voltage or difference voltage from the differential amplifier increases the current through the second impedance decreases thereby causing the battery voltage to increase due to a smaller voltage drop across the internal impedance of the battery. Thus the invention provides a means to maintain a substantially constant voltage across the first impedance (volatile memory) at the expense of reduced current flow through the second impedance (output circuit).

BRIEF DESCRIPTION OF THE DRAWINGS

FIG. 2 is a graph showing battery voltage versus time with and without a circuit according to the present invention;

FIG. 3 is a graph showing current through the output circuit versus time when utilizing a circuit according to the present invention.

DETAILED DESCRIPTION

As required, detailed illustrative embodiments of the invention are disclosed herein. These embodiments exemplify the invention and are currently considered to be the best embodiments for such purposes. However, it is to be recognized that other means for generating a reference voltage and other means for controlling current through the output circuit as a function of a voltage differential between the reference voltage and battery voltage could be utilized. Accordingly, the specific embodiments disclosed are representative in providing a basis for the claims which define the scope of the present invention.

As previously explained, the invention provides a means for controlling the current through an output circuit portion of an implantable human tissue stimulator in order to maintain a predetermined voltage differential across a volatile memory and control circuit (hereinafter referred to as the volatile memory) for as long a period of time as possible, the volatile memory and output circuit being connected in parallel across a battery. The invention discloses a means whereby a reference voltage derived from the battery is compared to the battery output voltage, a voltage proportional to their difference being used to bias a field-effect transistor (FET) connected in series with the output circuit. Thus as the voltage differential between the battery and the reference voltage decreases, the FET is biased so as to reduce the current flowing therethrough, thereby reducing current drain from the battery and causing the battery voltage across the volatile memory to remain constant.

Figure 1:
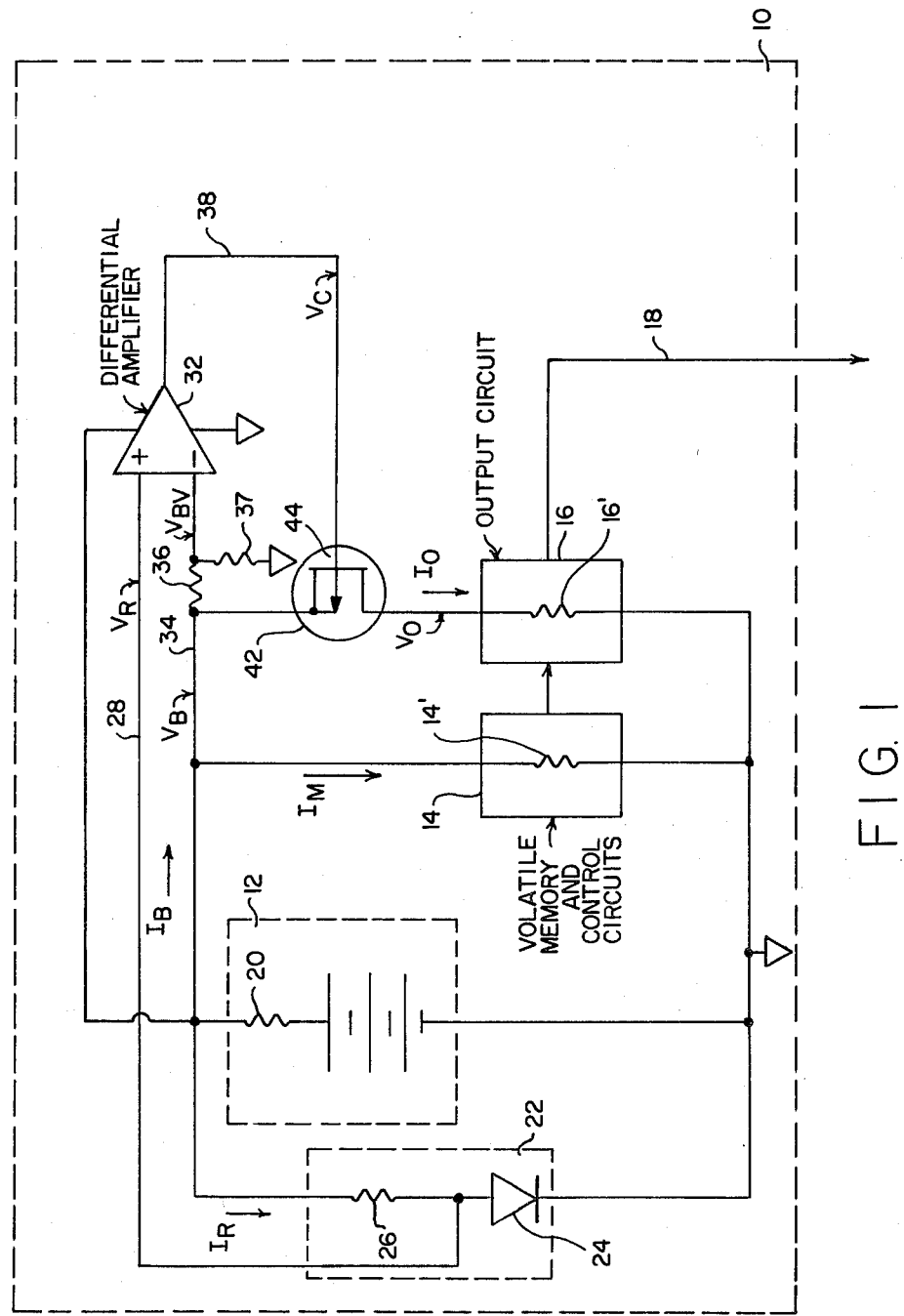
FIG. 1 is a schematic diagram of a circuit according to a first embodiment of the present invention.

Referring to FIG. 1, an implantable tissue stimulator 10 comprises a battery 12, a volatile memory 14 and output circuit 16, the volatile memory 14 and output circuit 16 being connected in parallel across the battery 12. The volatile memory 14 can be functionally represented with respect to the battery as a first resistance 14' and the output circuit 16 can be represented as second resistance 16'. As has been previously explained, the volatile memory 14 comprises a programmable memory which determines the frequency, duration and other characteristics of tissue stimulation pulses from the output circuit 16, the pulses appearing on an output line 18. The parameters describing the pulses are determined in accordance with programmed instructions provided to the volatile memory 14, and the amplitude of the pulses is determined by the voltage $V_O$ across the output circuit 16. As is well known in the medical sciences the repetition rate of the pulses is critical with respect to a patient and must meet predetermined criteria; however the amplitude of the pulses is normally set higher than needed in order to provide a safety factor for variations in the stimulation threshold of the living tissue. Thus a predetermined amplitude for the tissue stimulation pulses is established; however the pulses can be above that predetermined level without harming the patient. It is essential however, that the voltage across the volatile memory 14 not fall below a predetermined level in order to maintain integrity of the pulse-determining parameters stored within the volatile memory 14. In a typical tissue stimulator, the output circuit 16 draws approximately 10 times as much current as the volatile memory 14 ($I_O \approx 10 \, I_M$). If the battery 12 output voltage $V_B$ begins to drop, reduction of the current $I_O$ through the output circuit 16 will reduce the battery current $I_B$ through an internal resistance 20 of the battery, thereby causing the output voltage $V_B$ of the battery 12 appearing across the volatile memory 14 to increase.

Control of the current through the output circuit 16 as a function of the output voltage $V_B$ of the battery 12 is accomplished as follows. Referring again to FIG. 1, a reference voltage generator 22 comprising a forward biased diode 24 and a dropping resistor 26 is provided. A reference current $I_R$ which flows through the dropping resistor 26 and the diode 24 results in a substantially constant voltage drop across the diode 24, this voltage drop being represented by $V_R$ and being present on a reference voltage line 28. A differential amplifier 32 is provided, the differential amplifier 32 having a predetermined fraction of the battery output voltage $V_B$ present on output line 34 and as the other input the output $V_R$ from the reference voltage generator 22. Two biasing resistors 36 and 37 are chosen so that a battery voltage substantially equal to that of the minimum voltage required for proper operation of the volatile memory 14 results in a bias voltage $V_{BV}$ being substantially equal to the voltage drop across the diode 24. The differential amplifier 32 provides a control voltage output $V_C$ which appears on an output line 38, the control voltage $V_C$ being a function of the voltage differential between the reference voltage $V_R$ and the bias voltage $V_{BV}$. A P channel enhancement mode field-effect transistor (FET) 42 is connected in series between the output circuit 16 and the battery 12 although other types of transistors or circuits could be utilized. The gate electrode 44 of the FET 42 is connected to the differential amplifier output line 38. In the circuit described, the field-effect transistor 42 is acting as a variable resistance, the resistance increasing as the voltage differential between $V_{BV}$ and $V_R$ decreases.

In operation, continued use of the battery results in a gradual decrease in battery voltage $V_B$ due to a gradual increase in the internal resistance 20 of the battery 12. When $V_{BV}$ is higher than $V_R$, the output of the differential amplifier 32 is low, thereby keeping the FET 42 on. However, as soon as the value of $V_{BV}$ drops to a level substantially equal to that of $V_R$, then the output of the differential amplifier 32 begins to rise, thereby beginning to turn the FET 42 off so that the current $I_O$ flowing therethrough is reduced. This lowered $I_O$ lowers $I_B$ ($I_B = I_M + I_O$) and thereby reduces the voltage drop due to the internal impedance 20 of the battery and causes $V_B$ to remain high. Thus the output voltage $V_B$ of the battery is maintained somewhat constant as a result of gradually reducing $I_O$ which in turn reduces the amplitude of the output pulses from the output circuit 16. Thus $V_B$ is maintained at a higher level than it normally would be due to this reduced current through the output circuit 16.

The above-described effects can be seen diagrammatically by referring to FIGS. 2 and 3. As can be seen, during the first portion 50 of the battery voltage versus time curve the battery voltage $V_B$ decreases slightly as a function of time. At time $T_1$ and in the absence of a circuit as described above, the battery voltage $V_B$ would continue to decrease as shown by the dotted line 52. However by using the above described circuit, the battery voltage $V_B$ during the time between $T_1$ and $T_2$ remains substantially constant as shown at 54 because of the continually reduced current flowing to the output circuit 16 as represented by the current line 56 shown in FIG. 3. If the FET 42 is completely biased to cut off by the control voltage $V_C$ so that no current flows therethrough as indicated at time $T_2$, then the battery voltage $V_B$ continues to drop, however at a slower rate due to the lower current drain required by the volatile memory 14 as shown at 58.

Figure 4:
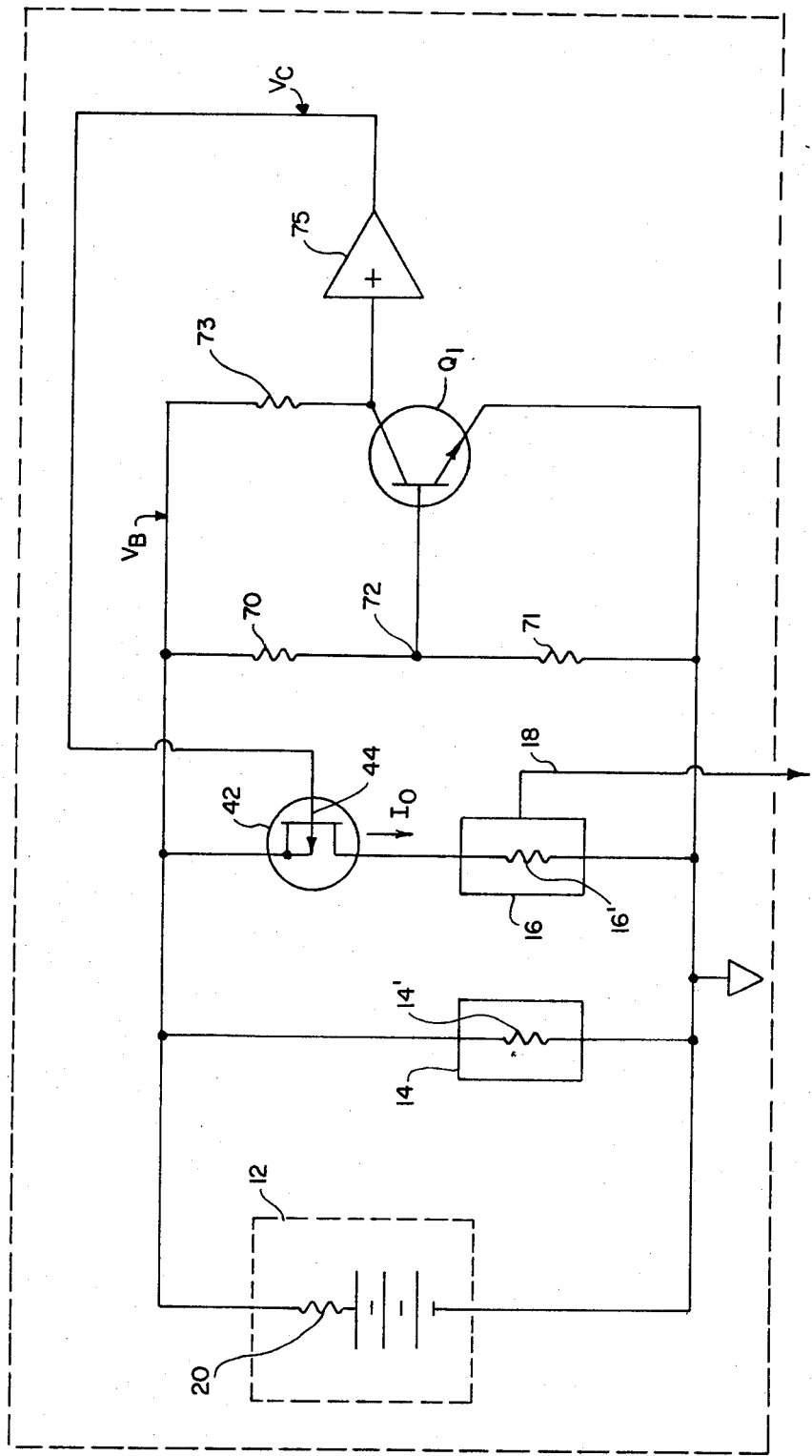
FIG. 4 is a schematic diagram of a further embodiment of the invention showing an alternate means of generating the control voltage.

Attention is now directed to FIG. 4 wherein a further embodiment of the invention is shown. First and second dropping resistors 70 and 71, respectively, are connected across the battery 12, their junction point 72 being connected to the control electrode of a transistor Q1. The emitter electrode of transistor Q1 is connected to ground. The collector electrode is connected to the battery 12 through a resistor 73, and to the input of an amplifier 75 whose output $V_C$ controls the FET 42.

In operation, dropping resistors 70 and 71 are chosen so that if $V_B$ is not less than a level as that represented in FIG. 2 at time $T_1$, Q1 is fully conductive. Therefore, the output of amplifier 75 is low, i.e., $V_C$ is low and the FET 42 is fully conductive. However, when the voltage $V_B$ is substantially equal to or below that represented in FIG. 2 at time $T_1$, the voltage at the junction 72 of dropping resistors 70 and 71 decreases. As a result Q1 is driven toward cutoff, resulting in an increased input to the amplifier 75. Thus $V_C$ increases, thereby reducing $I_O$ through the FET 42 and the output circuit 16.

Thus as one can appreciate, a circuit suitable for use in an implantable tissue stimulator has been described whereby the life of a volatile memory stimulator is extended at the expense of a safety factor in the amplitude of an output tissue stimulation pulse.

What is claimed is:

1. In an implantable human tissue stimulator having a volatile memory and control circuit means and an output circuit both of which are connected in parallel across a battery, said memory and control circuit means comprising a first resistance and said output circuit comprising a second resistance, the improvement comprising means for altering the ratio of current flowing through said second resistance with respect to current flowing through said first resistance as a function of said battery output voltage.

2. The improved stimulator of claim 1 in which said means for altering comprises:
   means for generating a substantially constant reference voltage;
   means for providing a control voltage related to a voltage difference between said reference voltage and said battery output voltage; and means for reducing current through said second resistance as a function of said control voltage.

3. The improved stimulator of claim 2 in which said means for reducing comprises:
   a transistor in series with said second resistance and said battery; and
   means for connecting the control electrode of said transistor to said control voltage whereby said control voltage controls current through said transistor.

4. The improved stimulator of claim 3 in which said transistor comprises a field-effect transistor (FET).

5. The improved stimulator of claim 1 in which said altering means comprises:
   means for providing a control voltage related to the output voltage of said battery; and
   means for reducing current through said second resistance as a function of said control voltage.

6. The improved stimulator of claim 5 wherein said means for providing comprises:
   a control transistor;
   means for applying a voltage related to said battery voltage to the base of said control transistor whereby current flow through said control transistor is related to said battery voltage; and
   means for generating a voltage related to said current flow through said control transistor, said voltage being related to said control voltage.

7. The improved stimulator of claim 6 wherein said control transistor is an npn transistor and said means for generating comprises:
   a dropping resistor connected in series between said control transistor collector and a positive terminal of said battery; and
   means for connecting said control transistor collector to a return terminal of said battery whereby the voltage at said control transistor collector comprises said voltage related to said current flow.

8. The improved stimulator of claim 7 wherein said means for reducing current comprises an FET in series with said second resistance.

9. In an implantable human tissue stimulator comprising a volatile memory and control circuit means having a first resistance and an output circuit having a second resistance, both of which are connected in parallel across a battery, a method of varying the ratio of current through said second resistance with respect to current through said first resistance, the steps comprising:
   generating a substantially constant reference voltage;
   providing a control voltage related to a voltage difference between said battery voltage and said reference voltage; and
   controlling current through said second resistance as a function of said control voltage.

10. The method of claim 9 in which said controlling step further comprises the step of biasing a transistor with said control voltage, said transistor being in series with said second resistance and said battery.

11. In an implantable human tissue stimulator having a voltage source driving a first load impedance and a second load impedance in parallel with said first load impedance, the improvement comprising:
    means for generating a reference voltage;
    means for providing a control voltage related to a voltage difference between said reference voltage and said voltage source; and
    means for controlling current through said second load impedance as a function of said control voltage.

12. The improved stimulator of claim 11 wherein said voltage source is a dc voltage source having positive and negative terminals and said means for generating comprises:
    a resistor; and
    a diode, said resistor and said diode being connected in series across said voltage source so that a voltage drop across said diode comprises said reference voltage.

13. The improved stimulator of claim 11 wherein said means for providing comprises a differential amplifier having a voltage related to said voltage source output voltage as a first input and said reference voltage as a second input, said differential amplifier providing an output voltage related to a difference between said first and second input voltages, said output voltage comprising said control voltage.

14. The improved stimulator of claim 11 wherein said means for controlling comprises a transistor in series with said second load impedance and said voltage source, and having its base electrode connected to said control voltage whereby current through said transistor is related to said control voltage.

15. The improved stimulator of claim 14 wherein said transistor is a field-effect transistor (FET).

* * * * *